US012527720B2

(12) United States Patent
Pai

(10) Patent No.: US 12,527,720 B2
(45) Date of Patent: Jan. 20, 2026

(54) WIRELESS IDENTIFICATION NEEDLE

(71) Applicant: RFID INTEGRATED MARKETING CO., LTD., Taichung (TW)

(72) Inventor: Tung-Sheng Pai, Taichung (TW)

(73) Assignee: RFID INTEGRATED MARKETING CO., LTD., Taichung (TW)

( * ) Notice: Subject to any disclaimer, the term of this patent is extended or adjusted under 35 U.S.C. 154(b) by 125 days.

(21) Appl. No.: 18/417,301

(22) Filed: Jan. 19, 2024

(65) Prior Publication Data

US 2024/0299246 A1 Sep. 12, 2024

(30) Foreign Application Priority Data

Mar. 9, 2023 (TW) ................................ 112202086
Mar. 9, 2023 (TW) ................................ 112202087
Mar. 13, 2023 (TW) ................................ 112202173

(51) Int. Cl.
*A61H 39/08* (2006.01)
*A61B 90/98* (2016.01)

(52) U.S. Cl.
CPC ........... *A61H 39/086* (2013.01); *A61B 90/98* (2016.02)

(58) Field of Classification Search
CPC ...... A61H 39/04; A61H 39/08; A61H 39/086; H04W 4/80
See application file for complete search history.

(56) References Cited

U.S. PATENT DOCUMENTS

2020/0353222 A1* 11/2020 Jaquez ................ A61B 5/1535

* cited by examiner

*Primary Examiner* — Todd J Scherbel
(74) *Attorney, Agent, or Firm* — Birch, Stewart, Kolasch & Birch, LLP

(57) ABSTRACT

A wireless identification needle includes an acupuncture needle and an electronic tag. The acupuncture needle includes a needle body, a needle tip provided at a front end of the needle body, and a needle handle provided at a rear end of the needle body. The electronic tag includes a substrate directly or indirectly connected with the needle handle, an antenna disposed with the substrate, and a radio frequency identification (RFID) chip electrically connected with two ends of the antenna. As a result, the wireless identification needle has a table structure, a reduced metal interference, and a long-distance identification capability.

5 Claims, 15 Drawing Sheets

WIRELESS IDENTIFICATION NEEDLE

BACKGROUND OF THE INVENTION

1. Field of the Invention

The present invention relates generally to a needle utensil, and more particularly to a wireless identification needle.

2. Description of the Related Art

Nowadays, medical institutions continuously strive to improve healthcare quality to avoid the occurrences of medical negligence and errors. Unfortunately, medical negligence and errors are still inevitable. Therefore, patient safety has always been an important issue for the World Health Organization (WHO) and healthcare service systems of many countries.

The scope of acupuncture treatment covers many aspects, including digestive system disorders, endocrine and metabolic diseases, gynecological issues, neurological and psychiatric disorders, musculoskeletal disorders, etc.

Acupuncture treatment involves inserting needles into subcutaneous tissue or muscles at specific areas of the human body to treat various diseases or relieve pain. Since the acupuncture needle needs to be in direct contact with internal tissue of the human body, the hygiene and safety of the acupuncture needle itself is very important. Insufficient hygiene of the needle may lead to unnecessary pathogen infections, causing secondary harm and posing a risk of hospital-acquired infections. Further, medical accidents caused by leaving needles inside the human body may occur from time to time. To avoid reuse of disposable needles, the management task of taking back, counting, and discarding the used needles are extremely important.

Conventional disposable acupuncture needles are typically made of stainless-steel material, having extremely fine needle bodies. Even in the handle area, the diameter is usually only around 1.2 millimeters. This poses a technical challenge for fixedly attaching a radio frequency identification (hereinafter referred to as "RFID") electronic tag to the needle. Particularly, when attempting to achieve the goal of long-distance identifying multiple acupuncture needles to enhance identification efficiency, the aforesaid goal may be difficultly achieved by using an ultrahigh frequency (UHF) RFID technology because the limitations of needle configuration and space are liable to result in the difficulty of constructing a UHF RFID antenna and the occurrence of the metal interference of the transmission and receipt of the antenna electromagnetic signal.

SUMMARY OF THE INVENTION

The present invention has been accomplished in view of the above-noted circumstances. It is an objective of the present invention to provide a wireless identification needle, which has a stable structure, can reduce metal interference, and possess the capability of long-distance identification.

To attain the above-mentioned objective, the present invention provides a wireless identification needle comprising an acupuncture needle and an electronic tag. The acupuncture needle includes a needle body, a needle tip provided at a front end of the needle body, and a needle handle provided at a rear end of the needle body. The electronic tag includes a substrate directly or indirectly connected with the needle handle, an antenna disposed with the substrate, and a radio frequency identification (RFID) chip electrically connected with two ends of the antenna. As a result, the wireless identification needle has a table structure, a reduced metal interference, and a long-distance identification capability.

BRIEF DESCRIPTION OF THE DRAWINGS

The present invention will become more fully understood from the detailed description given herein below and the accompanying drawings which are given by way of illustration only, and thus are not limitative of the present invention, and wherein.

DETAILED DESCRIPTION OF THE INVENTION

Figure 1:
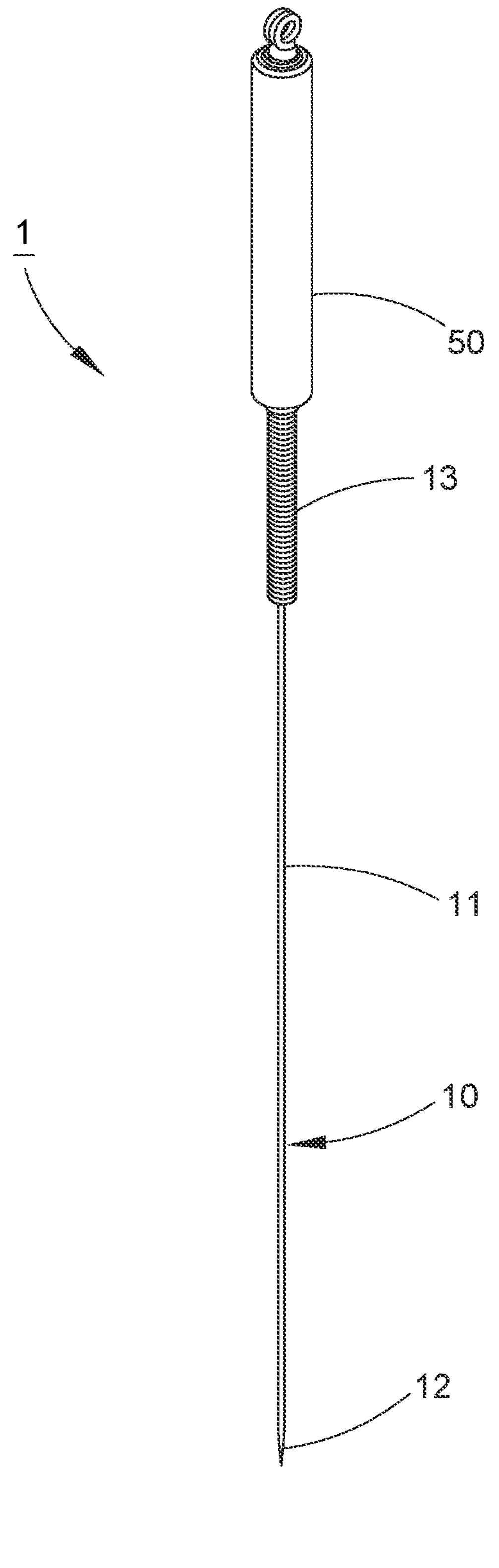
FIG. 1 is a perspective view of a wireless identification needle in accordance with a first embodiment of the present invention.
Figure 2:
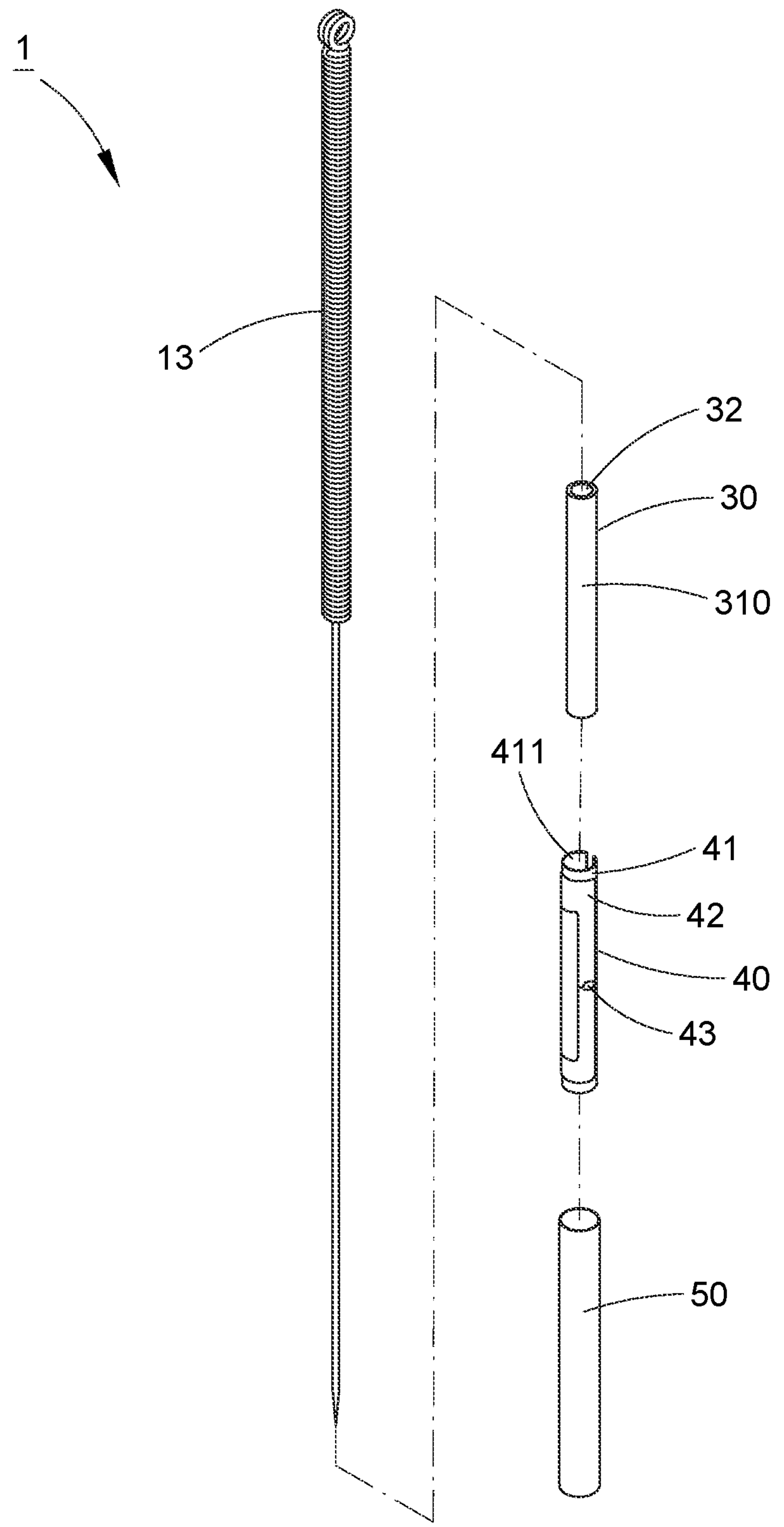
FIG. 2 is an exploded perspective view of the wireless identification needle of the first embodiment of the present invention.
Figure 3:
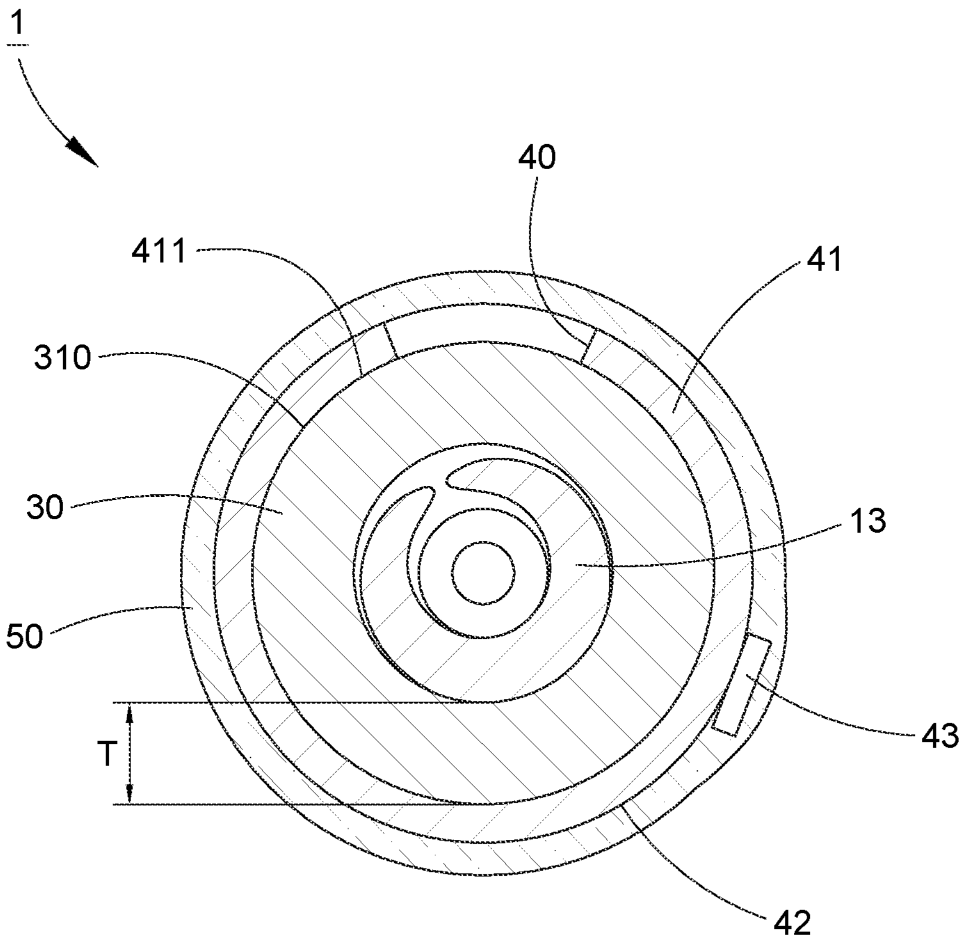
FIG. 3 is a cross-sectional view of the wireless identification needle of the first embodiment of the present invention.
Figure 4:
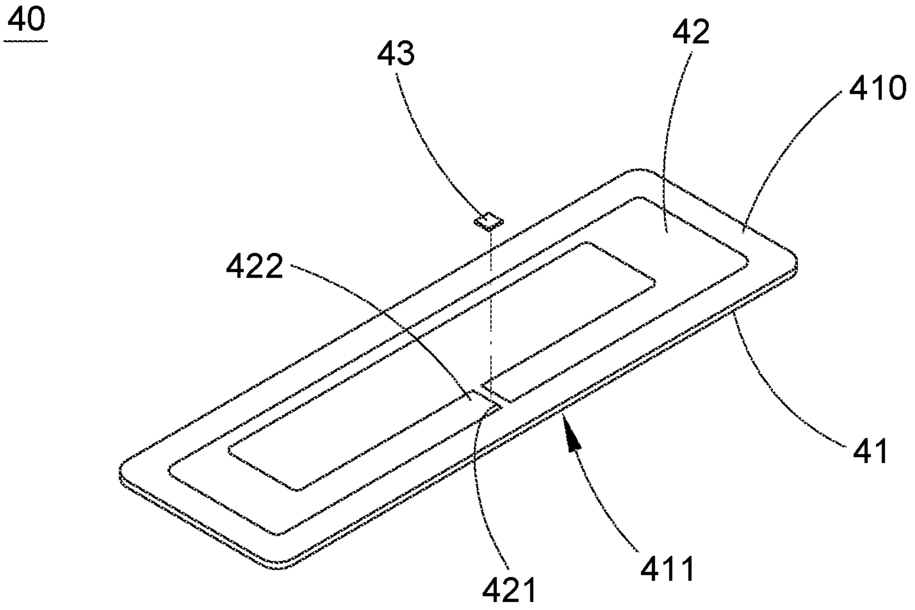
FIG. 4 is an exploded perspective view of an electronic tag of the wireless identification needle of the first embodiment of the present invention.

Hereunder five embodiments will be detailedly described with accompanying drawings for illustrating technical features and structure of the present invention. FIGS. 1-4 depict a wireless identification needle 1 provided in accordance with a first preferred embodiment of the present invention. The wireless identification needle 1 is composed of an acupuncture needle 10, an expansion sleeve 30, an electronic tag 40, and a protective sheath 50.

The acupuncture needle 10 includes a needle body 11, a needle tip 12 provided at the front end of the needle body 11, and a needle handle 13 provided at the rear end of the needle body 11. The needle handle 13 is formed by winding a wire, and has an outer diameter greater than the outer diameter of the needle body 11. The acupuncture needle 10 is integrally formed from a metal wire material, such as stainless-steel wire material. For illustrative convenience, the term "front" used in the present description and claims refers to the bottom side of FIG. 1, and the term "rear" refers to the top side of FIG. 1. In another embodiment of the present invention, the needle handle 13 may be injection-molded from plastic material in such a way that needle handle 13 encases the needle body 11. In another embodiment of the present invention, the needle handle 13 may have a thickness same as that of the needle body 11.

The expansion sleeve 30 has a sleeve hole 32 for the insertion of the needle handle 13 therethrough, and is configured as having a separation thickness T of about 0.5 mm between the wall of the sleeve hole 32 and the outer circumference 310 of the expansion sleeve 30. The expansion sleeve 30 may be made of insulating material, soft rubber material, and/or heat-shrinkable material. Because the expansion sleeve 30 is made of elastic material, the sleeve hole 32 can be firmly and tightly sleeved onto the needle handle 13. The wall of the sleeve hole 32 may be fixed to the needle handle 13 by adhesive, or the expansion sleeve 30 may be injection-molded from plastic material in a way that the expansion sleeve 30 encases the needle handle 13 therein.

The electronic tag 40 includes a substrate 41 connected with the needle handle 13, an antenna 42 disposed on an outer surface 410 of the substrate 41, and a radio frequency identification (RFID) chip 43 electrically connected with two ends of the antenna 42. The substrate 41 is a flexible insulating sheet, preferably made of polyimide (PI) material, and has a rectangular shape. The inner surface 411 of the substrate 41 is coated with adhesive, allowing the substrate 41 to be wrapped and adhered around the outer circumference 310 of the expansion sleeve 30. In this way, the substrate 41 is indirectly connected with the needle handle 13. That is, the expansion sleeve 30 is provided between the needle handle 13 and the substrate 41. In the present invention, the term "indirectly connected" means that an element, such as the substrate 41, is connected with another element, such as the needle handle 13, through or by means of one or more other elements, and the term "directly connected" refers to that one element, such as the substrate 41, is in direct connection with another element, such as the needle handle 13, without having other components therebetween. The antenna 42 is made of conductive material and is applied to the outer surface 410 of the substrate 41. It can be produced by etching the surface of a commonly used flexible circuit board, such as a metal foil (e.g., copper foil or aluminum foil). The antenna 42 has a rectangular annular shape with a slit-shaped notch 421, and the two ends 422 of the antenna 42 are located at two lateral sides of the notch 421. The RFID chip 43 is an ultra-high-frequency radio frequency identification chip (UHF RFID) electrically connected with the two ends 422 of the antenna 42. In another embodiment, the antenna 42 may be disposed on the inner surface 411 of the substrate 41 or inside the substrate 41 (i.e., the antenna 42 is located between the inner surface 411 and the outer surface 410). The shape or structure of the antenna 42 may be modified in accordance with the actual need, and the shape of the antenna 42 is not limited to be rectangular. The RFID chip 43 may be configured as using a suitable frequency band as needed.

The protective sheath 50 completely encases the electronic tag 40 and the expansion sleeve 30 therein, such that the protective sheath 50 is fixedly mounted on the needle handle 13. This ensures the isolation and protection of the antenna 42 and the RFID chip 43 from the external environment. The protective sheath 50 may be made of heat-shrinkable material to enhance the structural stability of the electronic tag 40 and the expansion sleeve 30 when they are mounted on the needle handle 13. However, in the case that the electronic tag 40 can be firmly coupled to the expansion sleeve 30, the protective sheath 50 may be omitted.

Because the separation thickness T of the expansion sleeve 30 separates the antenna 42 of the electronic tag 40 from the acupuncture needle 10 at a certain gap and the outer circumference of the expansion sleeve 30 allows the antenna 42 on the substrate 41 to fully extend, the antenna 42 can resonate with the electromagnetic wave signals reflected by the acupuncture needle 10. This allows a reader (not shown) to read the identification code of the RFID chip 43 from a long distance under the resistance to metal interference, thereby achieving the goal of identifying the wireless identification needles 1 so as to facilitate the task of counting, controlling, and taking back the used wireless identification needles 1.

Experimental results show that the expansion sleeve 30 is preferably configured as having a separation thickness T equal to or greater than 0.4 mm, thereby providing a sufficient gap for interference resistance between the antenna 42 and the acupuncture needle 10. Taking a UHF RFID system planned for a hospital and using a frequency range from 922 MHz to 928 MHz for example, the theoretical reading distance measured through a reading distance test for the wireless identification needle 1 is approximately 1.1 meters to 1.2 meters. This confirms that the antenna 42 is not affected by the metal material of the acupuncture needle 10. Moreover, because of the increased device power, the actual reading distance will be in average about 1.5 times the theoretical reading distance. As such, the actual reading distance of the wireless identification needle 1 will reach about 1.65 meters to 1.8 meters at the frequency of 922 MHz to 928 MHz, meeting the control requirements of using and taking back the hospital needles.

Figure 5:
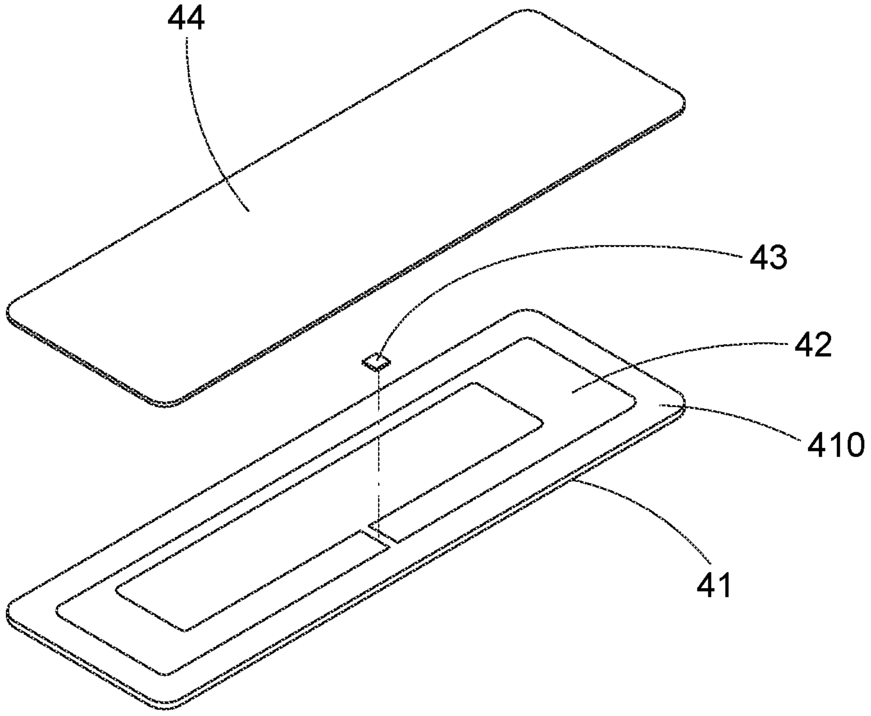
FIG. 5 is an exploded perspective view of an electronic tag of a wireless identification needle in accordance with a second embodiment of the present invention.
Figure 6:
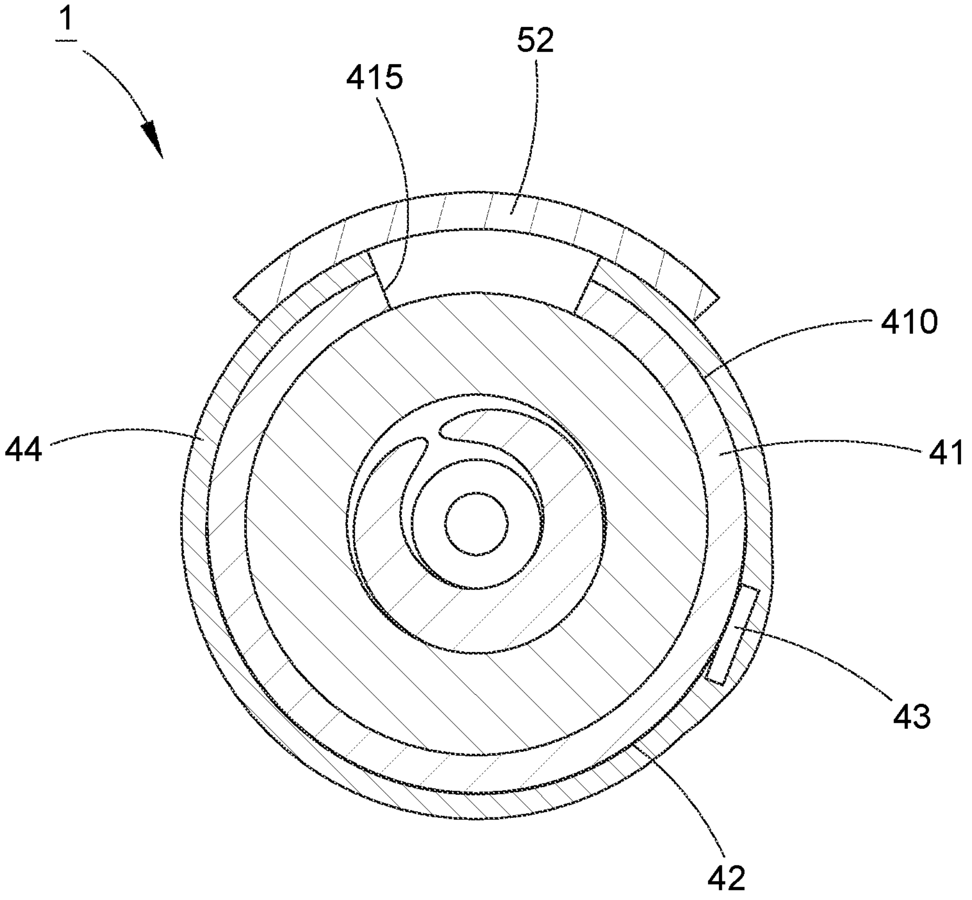
FIG. 6 is a cross-sectional view of the wireless identification needle of the second embodiment of the present invention.

FIGS. 5 and 6 show a wireless identification needle 1 provided in accordance with a second preferred embodiment of the present invention. An insulating protective film 44, such as PET film, PI film, is adhered on the outer surface 410, such that the antenna 42 and the RFID chip 43 are covered by the insulting protective film 44 and isolated from the external environment. In addition, to prevent the two lateral edges 415 of the substrate 41 from warpage due to glue detachment or other causes after the substrate 41 is wrapped in a roll manner, a patch 52 may be applied to cover the two lateral edges 415 of the substrate 41. While the patch 52 does not completely encase the electronic tag 40 like the protective sheath 50 does, it still achieves the effect of securing the electronic tag 40. However, in the case that the electronic tag 40 can be securely coupled to the expansion sleeve 30, the patch 52 may be omitted.

Figure 7:
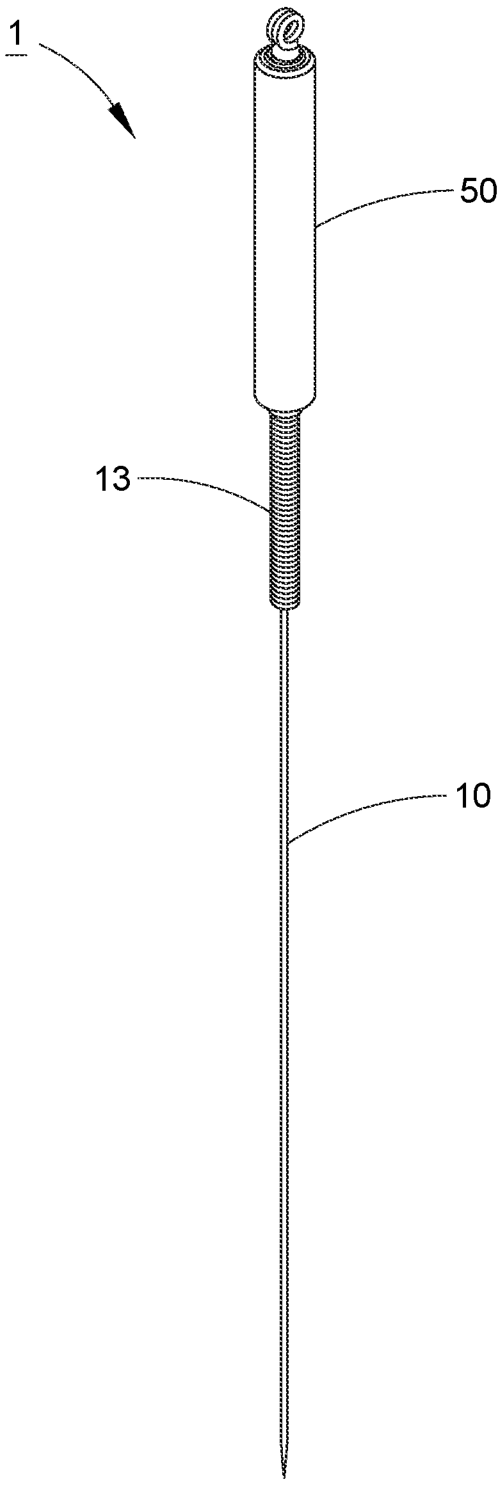
FIG. 7 is a perspective view of a wireless identification needle in accordance with a third embodiment of the present invention.
Figure 8:
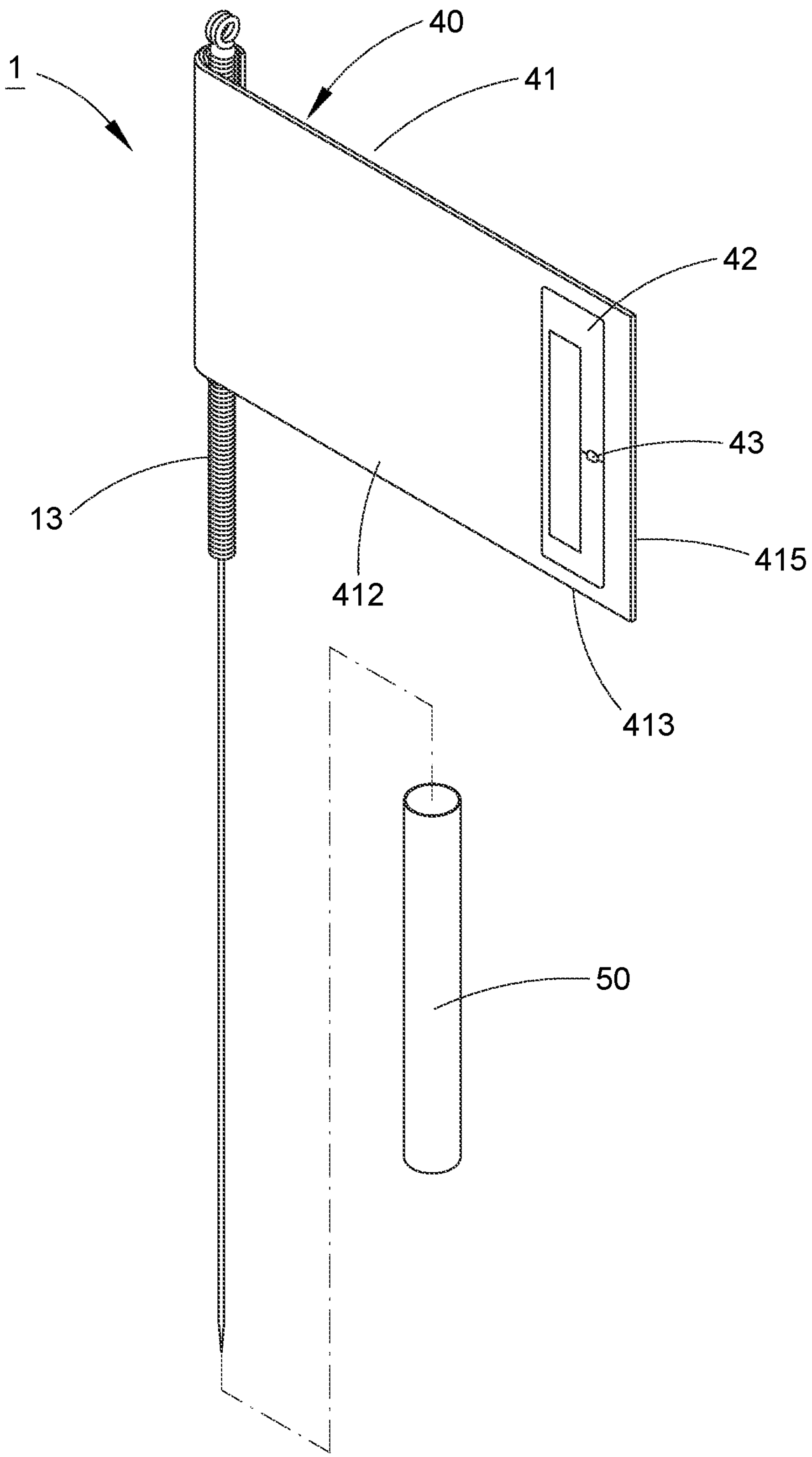
FIG. 8 is an exploded perspective view of the wireless identification needle of the third embodiment of the present invention.
Figure 9:
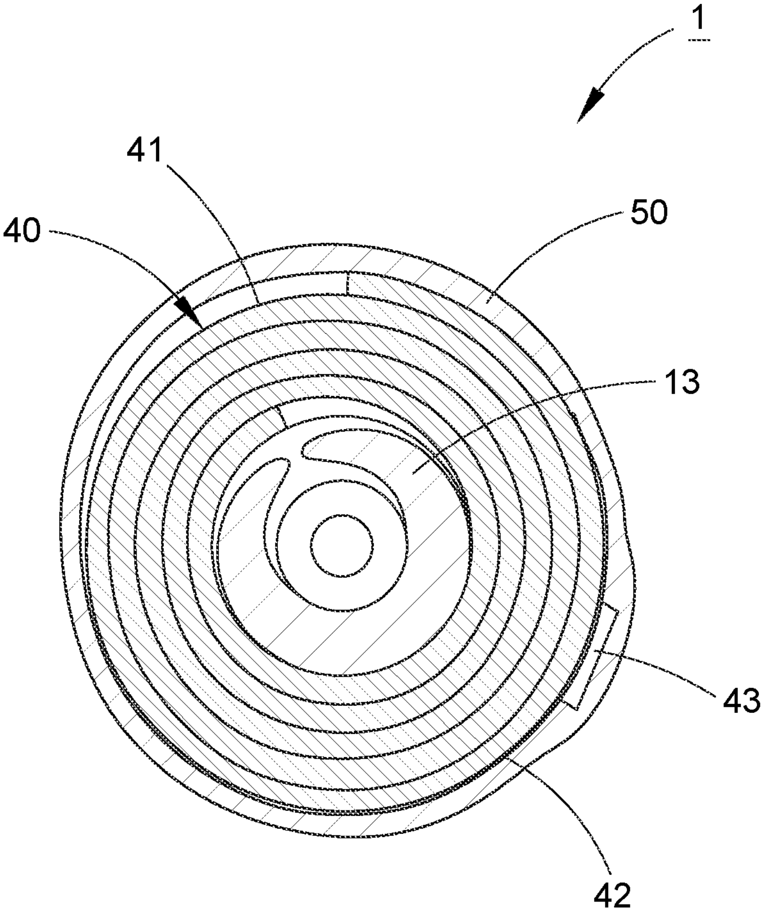
FIG. 9 is a cross-sectional view of the wireless identification needle of the third embodiment of the present invention.

FIGS. 7 to 9 show a wireless identification needle 1 provided in accordance with a third preferred embodiment of the present invention. The wireless identification needle 1 is composed of an acupuncture needle 10, an electronic tag 40, and a protective sheath 50, omitting the expansion sleeve 30 used in the first embodiment. The substrate 41 of the electronic tag 40 has a separation section 412 connected to the needle handle 13, and a sensing section 413 extending from the separation section 412. The antenna 42 is disposed at the sensing section 413. The substrate 41 is directly wrapped and coiled around the outer circumference of the needle handle 13. After the substrate 41 is coiled around the needle handle 13, the separation section 412 is situated between the needle handle 13 and the sensing section 413, and the distance between the outermost sensing section 413 and the outer circumference of the needle handle 13 becomes the separation thickness T. The protective sheath 50 encases the electronic tag 40 therein.

By means of the separation thickness T formed by the coiled roll of the substrate 41 and provided with at least 0.4 mm or more, the antenna 42 is separated from the acupuncture needle 10 by a certain distance. The separation section 412, after it is coiled as a roll manner, achieves the same effect as the expansion sleeve 30 in the first embodiment, and allows the antenna 42 on the sensing section 413 to be fully extended, thereby achieving the objectives of the present invention.

In this embodiment, the theoretical reading distance measured through a reading distance test for the wireless identification needle 1 is approximately 0.65 meters to 0.68 meters, and the actual reading distance will reach about 0.97 meters to 1.05 meters, still meeting the control requirements of using and taking back the hospital needles.

Figure 10:
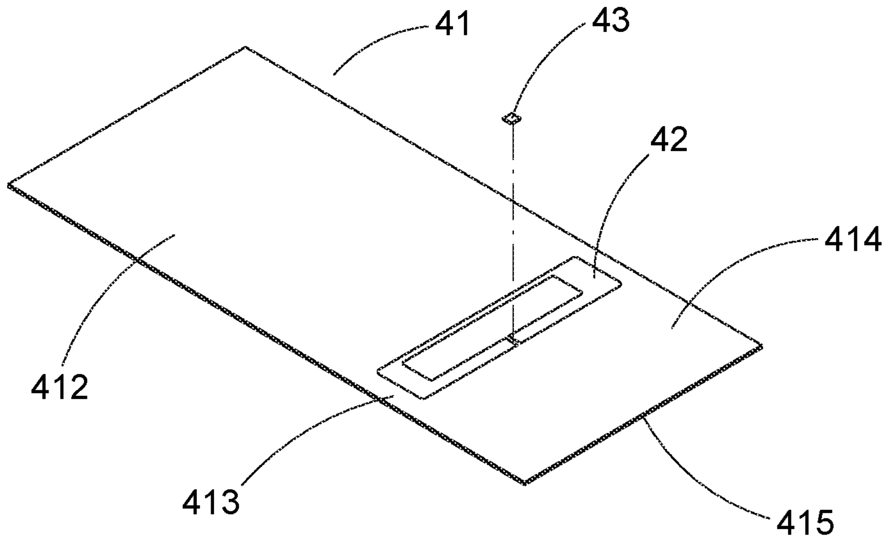
FIG. 10 is an exploded perspective view of an electronic tag of a wireless identification needle in accordance with a fourth embodiment of the present invention.
Figure 11:
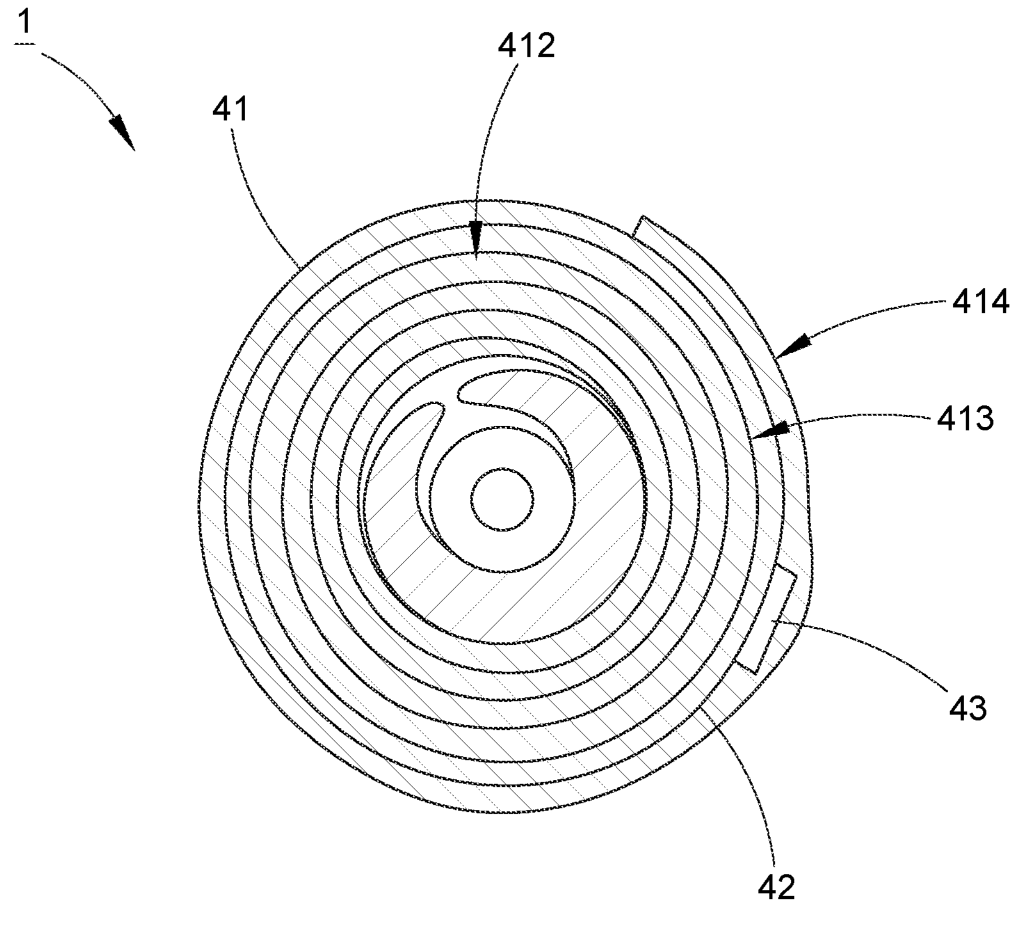
FIG. 11 is a cross-sectional view of the wireless identification needle of the fourth embodiment of the present invention.
Figure 12:
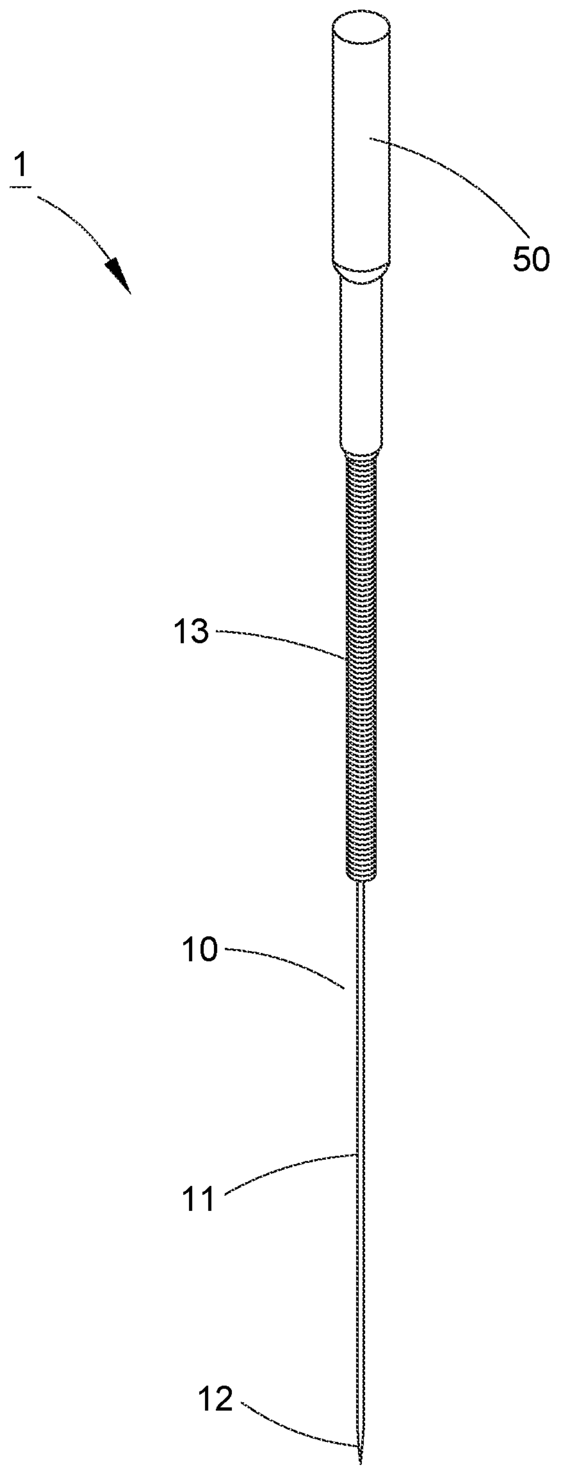
FIG. 12 is a perspective view of a wireless identification needle in accordance with a fifth embodiment of the present invention.
Figure 13:
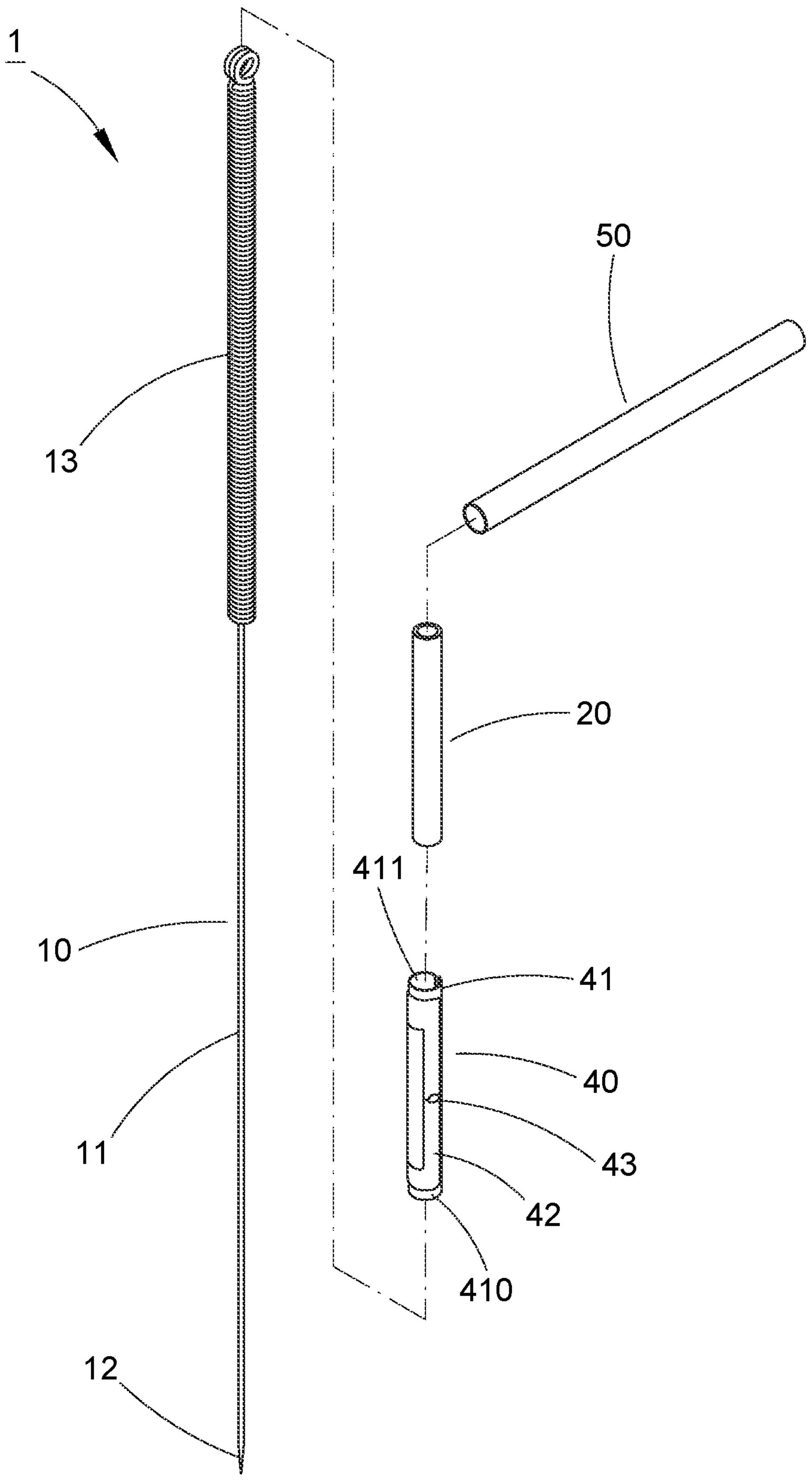
FIG. 13 is an exploded perspective view of the wireless identification needle of the fifth embodiment of the present invention.
Figure 14:
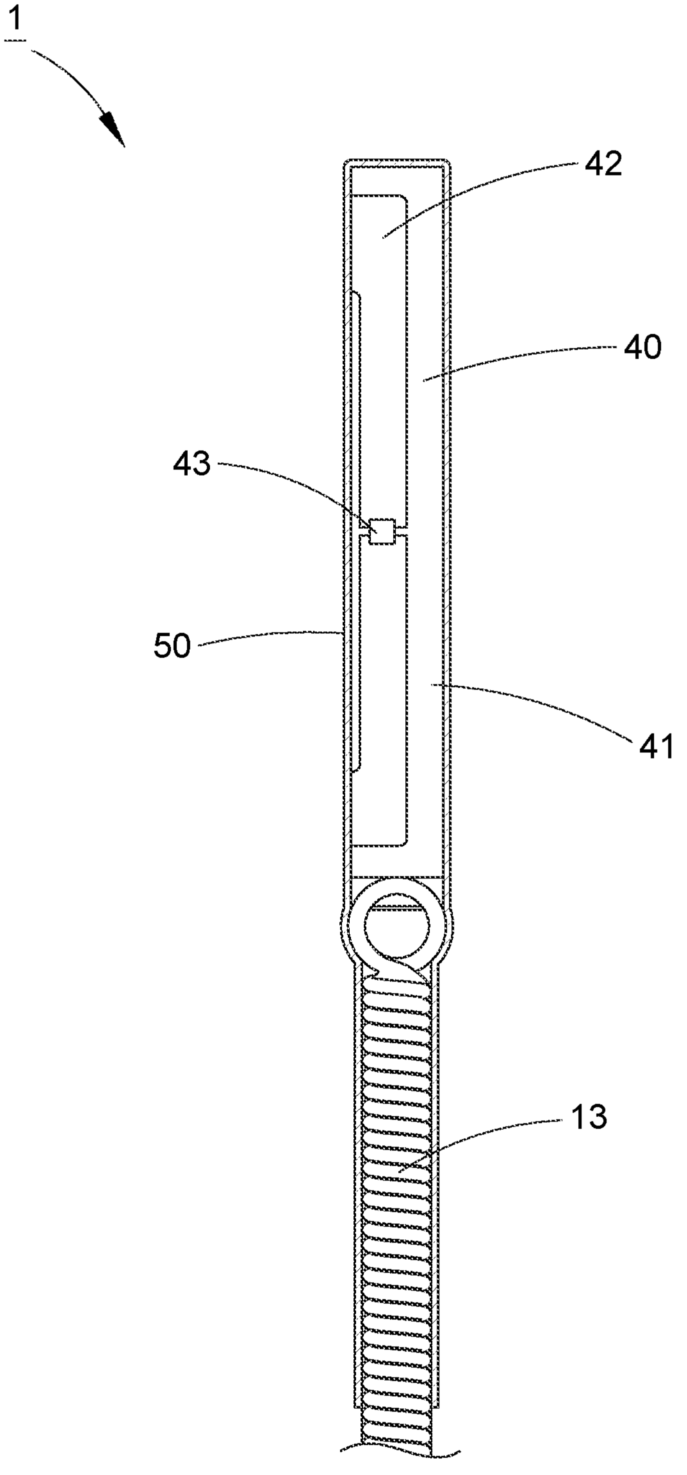
FIG. 14 is a longitudinally cross-sectional view of the wireless identification needle of the fifth embodiment of the present invention.
Figure 15:
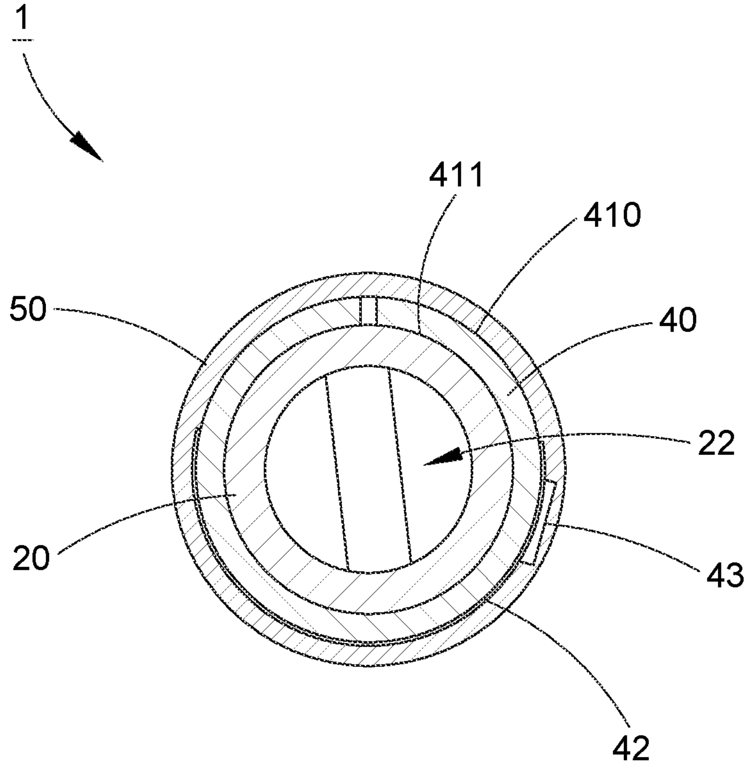
FIG. 15 is a transversely cross-sectional view of the wireless identification needle of the fifth embodiment of the present invention.

FIGS. 10 and 11 show a wireless identification needle 1 provided in accordance with a fourth preferred embodiment of the present invention. In addition to the separation section 412 and the sensing section 413, the substrate 41 of the electronic tag 40 further includes a covering section 414 extending from the sensing section 413. After the substrate 41 is wrapped around the needle handle 13 in serval turns, the covering section 414 covers the antenna 42 and the RFID chip 43 on the sensing section 413. In this way, the covering section 414 achieves the same effect as the protective sheath 50 in the third embodiment, isolating and protecting the antenna 42 and the RFID chip 43 from the external environment.

FIGS. 12 to 15 show a wireless identification needle 1 provided in accordance with a fifth preferred embodiment of the present invention. The wireless identification needle 1 is composed of an acupuncture needle 10, a liner 20, an electronic tag 40, and a protective sheath 50. The liner 20 is provided at a position behind the needle handle 13 at a distance and is made of plastic material in a tubular shape. The part inside the outer peripheral of the liner 20 is defined as a signal response space 22. The substrate 41 of the electronic tag 40 is wrapped and adhered around the outer peripheral of the liner 20. The rear section of the protective sheath 50 completely encases the electronic tag 40 and the liner 20 therein, and the front section of the protective sheath 50 covers over at least a part of the needle handle 13, such that the liner 20 and the electronic tag 40 are firmly coupled to the needle handle 13 via the protective sheath 50. This structure shows another example of the indirect connection between the substrate 41 of the electronic tag 40 with the needle handle 13. In another embodiment, the liner 20 may be rod-shaped.

Since the liner 20 can support the substrate 41 to allow the antenna 42 to be fully extended, it achieves the same effect as the expansion sleeve 30 in the first embodiment. The cross-sectional circumferential length of the liner 20 is greater than the cross-sectional circumferential length of the needle handle 13, resulting in that the cross-sectional circumferential length of the electronic tag 40 will be greater than the cross-sectional circumferential length of the needle handle 13. This design creates a resonant cavity in the signal response space 22, providing resistance to metal interference. In another aspect, the theoretical reading distance measured through a reading distance test for the wireless identification needle 1 in this embodiment is approximately 1.26 meters to 1.38 meters, and the actual reading distance will reach about 1.89 meters to 2.07 meters, meeting the control requirements of using and taking back the hospital needles. Moreover, in the case that the substrate 41 of the electronic tag 40 is made of a material with sufficient strength, there is no need to provide the liner 20 to allow the antenna 42 to be fully extended. Alternatively, as shown in the third embodiment, the substrate 41 in this embodiment may be configured having a sensing section 413 and a separation section 412 extending from the sensing section 413. The antenna 42 is disposed at the sensing section 413. In this way, after the substrate 41 is rolled up, the separation section 412 is covered by the sensing section 413. As a result, the separation section 412 can replace the function of the liner 20.

Based on the above-mentioned technical features, various modifications to the structure of the wireless identification needle 1 may be made. For example, if the diameter of the needle handle 13 is large enough, the expansion sleeve 30 or the separation section 412 may not be needed. In the third or fourth preferred embodiment, the electronic tag 40 may be equipped with the protective sheath 50 or the patch 52. In this design, the patch 52 is applied only to one lateral edge 415 of the substrate 41 after the substrate 41 is rolled up. Such variations are not to be regarded as a departure from the scope of the invention, and all such modifications as would be obvious to one skilled in the art are intended to be included within the scope of the following claims.

What is claimed is:

1. A wireless identification needle, comprising:

an acupuncture needle comprising a needle body, a needle tip provided at a front end of the needle body, and a needle handle provided at a rear end of the needle body;

an electronic tag comprising a substrate indirectly wrapped around an outer circumference of the needle handle, an antenna disposed with the substrate and provided with two ends, and a radio frequency identification chip electrically connected with the two ends of the antenna; and an expansion sleeve disposed between the needle handle and the substrate; the expansion sleeve has a sleeve hole into which the needle handle extends; the substrate covers an outer circumference of the expansion sleeve.

2. The wireless identification needle as claimed in claim 1, further comprising a patch covering at least one lateral edge of the substrate.

3. The wireless identification needle as claimed in claim 1, further comprising a protective sheath encasing the electronic tag.

4. A wireless identification needle, comprising:

an acupuncture needle comprising a needle body, a needle tip provided at a front end of the needle body, and a needle handle provided at a rear end of the needle body; and an electronic tag comprising a substrate directly wrapped around an outer circumference of the needle handle, an antenna disposed with the substrate and provided with two ends, and a radio frequency identification chip electrically connected with the two ends of the antenna;

wherein the substrate comprises a separation section and a sensing section extending from the separation section;

the antenna is disposed at the sensing section, and after the substrate is wrapped around the needle handle, the separation section is positioned between the needle handle and the sensing section.

5. The wireless identification needle as claimed in claim 4, wherein the substrate further comprises a covering section extending from the sensing section; after the substrate is wrapped around the needle handle, the sensing section is positioned between the separation section and the covering section.

* * * * *